US006296869B1

(12) United States Patent
Crotty et al.

(10) Patent No.: US 6,296,869 B1
(45) Date of Patent: Oct. 2, 2001

(54) ADHESIVE COSMETIC PATCH CONTAINING ALPHA OR BETA HYDROXY ACIDS

(75) Inventors: Brian Andrew Crotty, Branford; Craig Stephen Slavtcheff, Guilford; Alexander Paul Znaiden, Trumbull, all of CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/426,549

(22) Filed: Oct. 22, 1999

Related U.S. Application Data

(60) Provisional application No. 60/146,509, filed on Jul. 30, 1999.

(51) Int. Cl.[7] ........................................ A61K 9/70

(52) U.S. Cl. .......................... 424/448; 424/401; 424/443; 424/444; 424/445; 424/446; 424/447; 424/449; 424/484; 514/458; 514/474; 514/844; 514/859

(58) Field of Search .................................... 424/448, 401, 424/443, 444, 445, 446, 447, 449, 484; 514/458, 474, 844, 859

(56) References Cited

U.S. PATENT DOCUMENTS

| | | | |
|---|---|---|---|
| 4,891,228 | | 1/1990 | Thaman et al. . |
| 5,425,938 | * | 6/1995 | Crotty et al. . |
| 5,620,694 | | 4/1997 | Girardot . |
| 5,814,662 | * | 9/1998 | Crotty et al. . |
| 5,935,596 | * | 8/1999 | Crotty et al. . |

FOREIGN PATENT DOCUMENTS

| | | | |
|---|---|---|---|
| 56120577 | * | 7/1981 | (EP) . |
| 2734574 | * | 11/1996 | (FR) . |
| 98/52538 | | 11/1998 | (WO) . |

* cited by examiner

*Primary Examiner*—Raj Bawa
(74) *Attorney, Agent, or Firm*—Milton L. Honig

(57) ABSTRACT

A dermal patch is provided which includes a substrate formed of a hydrophobic and hydrophilic fiber mixture, and a hydrogel adhesive deposited onto the substrate. The adhesive contains an alpha or beta hydroxy acid. The patch is applied to skin for treating the signs of aging, especially around areas of the eye.

10 Claims, No Drawings

ADHESIVE COSMETIC PATCH CONTAINING ALPHA OR BETA HYDROXY ACIDS

This application is a provisional of No. 60,146,509 filed Jul. 30, 1999.

BACKGROUND OF THE INVENTION

1. Field of the Invention

The invention concerns an adhesive patch for delivering cosmetic chemicals to improve the youthful appearance of skin.

2. The Related Art

New treatments are regularly being reported for the eradication of fine lines and wrinkles on human skin. Alpha and beta hydroxy acids have been the leading actives to suppress the signs of aging. A key disclosure is U.S. Pat. No. 5,091,171 (Yu et al.) reporting on the performance of alpha hydroxy acids and a variety of related structures. Formulation of these actives remains difficult. Perhaps due to their acidity, products containing these actives tend to sting, cause redness and generally irritate the skin. Especially vulnerable are areas near the eyes. Facial typography and consumer washing habits tend to direct facially applied chemicals toward the eye.

Most common delivery vehicles for hydroxy acids are cream and lotion formulations. Their mobility inherently carries actives to non-target areas of the skin. Precise application is a problem.

Towelettes have been utilized to deliver salicylic and other hydroxy acids. For instance, U.S. Pat. No. 5,620,694 (Girardot) reports a dual textured treatment pad impregnated with medicated, cleansing or cosmetic compositions. Examples of anti-acne agents disclosed as possible components include lactic and glycolic acids. Another related disclosure is U.S. Pat. No. 4,891,228 (Thaman et al.) describing medicated cleansing pads formulated with salicylic acid.

Disposable wipes are reported in WO 98/52538 (Wagner et al.). These wipes deliver a combination of a lathering surfactant and a conditioning emulsion on a substantially dry substrate. A quite large range of additional ingredients including anti-wrinkle and anti-acne actives are reported. Among these are salicylic and hydroxy acids.

In most instances, wipes are only slightly better than liquid formulations in precisely targeting affected areas of the skin without spillover. Better carrier systems are necessary.

Accordingly, it is an object of the present invention to provide a delivery system for hydroxy acids which targets their deposition in a more efficient, less irritating manner.

Another object of the present invention is to provide a delivery system for hydroxy acids which is at least as effective as liquid carriers in eliminating the signs of aging, especially treatment of age spots, fine lines and wrinkles.

These and other features and advantages of the present invention will become more readily apparent from consideration of the following summary and detailed description.

SUMMARY OF THE INVENTION

A dermal adhesive strip is provided which includes:

(i) a flexible substrate formed of hydrophobic and hydrophilic fibers, in a respective ratio of 2:1 to 1:2; and (ii) a hydrogel adhesive deposited on a major surface of the flexible substrate, the adhesive containing an alpha- or beta-hydroxy acid.

DETAILED DESCRIPTION OF THE INVENTION

Now it has been discovered that alpha and beta hydroxy acids can be delivered to human skin in a highly targeted manner through the intermediacy of a dermal patch. More specifically, the dermal patch carries the hydroxy acids in a hydrogel adhesive positioned on a flexible substrate. The substrate must be a substance formed of hydrophobic and hydrophilic fibers, in a respective ratio of 2:1 to 1:2, preferably from about 1.5:1 to about 1:1.5, optimally about 1:1 by weight.

Flexible substrates of the present invention may either be woven or non-woven. The hydrophilic fibers of the substrate may be natural materials such as cellulosics selected from the group consisting of wood pulp, cotton, hemp, jute, flax and fiber mixtures thereof. Semi-synthetic and synthetic hydrophilic fibers such as rayon and hydrophilic polyesters may also be employed. The most preferred fiber is rayon. Hydrophobic fibers normally are synthetic plastics of sufficiently high molecular weight to melt above about 20° C., preferably above 50° C., selected from the group consisting of polyvinyl acetate, polyacrylic, polymethacrylic, polyamide, styrene copolymers, hydrophobic polyester, polyolefin, polyurethane, polyvinylchloride, inorganics (e.g. lass) and combinations thereof. Examples of these include acrylonitrile-based acrylics, nylons (e.g. nylon 6, nylon 66, nylon 610), polyethylene terephthalate, polypropylene and polyethylene.

Preferably fiber diameters may range from about 0.1 to about 50 $\mu$m, but higher or lower sizes may be suitable depending on fiber type and binder systems.

The term "hydrophilic" is used to describe materials which are wetted by water (i.e. the surfaces of the materials have contact angles with water less than 90°). By contrast, the term "hydrophobic" is used to describe materials which are not wetted by water (i.e. the surfaces of hydrophobic materials have contact angles with water greater than 90°). While it is relatively straight forward to determine contact angle directed by optical measurements at the liquid-solid interface between water and flat solid surfaces, it is relatively complex to obtain contact angle between individual fibers or filaments in water. Yet these measurements may be accomplished utilizing a Wilhelmy balance principal. Relative hydrophilic/hydrophobic nature of individual fibers or filaments can be calculated through the fiber wettability values. See the article titled "Methodology For Studying The Wettability Of Filaments" by Bernard Miller and Raymond A. Young, Textile Research Journal, May 1975.

Fiber material which ordinarily has been classified as hydrophobic or hydrophilic may be treated with a surface coating to alter its water philicity properties. Hydrophilic properties may be imparted by coating with a surfactant. These materials may include alkyl ether sulfates, alkyl benzene sulfonates, fatty acid soaps, betaines, polyalkoxylated derivatives of sorbitan, of $C_6$–$C_{20}$ alcohols or of $C_6$–$C_{20}$ fatty acids, polyglycerol fatty acid esters and combinations thereof. Alternatively, hydrophilic properties may be applied to a hydrophobic fiber core by treatment of the latter with a coating of a silicone oil (high molecular weight dimethicone) or a fluorine containing substance.

Patches of the present invention normally will not be of the type requiring film formation by evaporation of water from a hydrogel deposit on the substrate. They are not intended for keratotic pore plug removal through peel-off from skin.

Generally, non-woven substrates are those prepared by air-laying or water-laying processes in which the fibers or filaments are first cut to the desired length from long strands, passed into water or airstreams, and then deposited onto a screen or mesh through which the fiber-laid in air or water is passed. The resulting non-woven layer, regardless of its method or production or composition, is then subjected to at least one of several types of bonding operations to anchor the individual fibers together to form a self-sustaining web. Specific processes for preparing the non-woven substrate include hydroentanglement, thermal bonding and combinations of these processes.

Optionally, the non-woven substrate may be treated with a suitable polymeric resin or binder in order to fortify the bonding of the fibers. Examples of such resins or binders include those comprising monomers selected from the group consisting of styrene monomers, derivatized styrene monomers, butadiene monomers, derivatized butadiene monomers and mixtures thereof. A most preferred substrate is EW-8092 available from the Japan Vilene Company.

A hydrogel adhesive is deposited on a major surface of the flexible substrate. Hydrogels are defined as coherent, three-dimensional aqueous polymer systems capable of absorbing water without liquefying. Generally the amount of water within the hydrogel may range from about 20 to about 95%, preferably from about 30 to about 90%, more preferably from about 45 to about 85%, optimally from at least 50 to 80% by weight. Illustrative of hydrogel adhesives are gelatins, polysaccharides, polyacrylamides, polyacrylates, polyvinylpyrrolidone, polyalkylene oxides, mixtures of the aforementioned polymers and mixtures of monomers forming the aforementioned polymers into copolymers. These polymers may be crosslinked (graft or free-radical induced) or non-crosslinked. Specific polymers include polyacrylamide, polyhydroxyethylmethacrylate, poly(2-acrylamido-2-methylpropanesulfonic acid), polyacrylic acid, polyvinylpyrrolidone, polyvinylalcohol and mixtures thereof. Most preferred are polyacrylics.

The hydrogel adhesive and flexible substrate may be present in relative weight ratios of from about 50:1 to about 1:50, preferably from about 10:1 to about 1:10, optimally from about 2:1 to about 1:2 by weight.

Suspended within the adhesive is an alpha- or beta-hydroxy carboxylic acid. The term hydroxy carboxylic acid is meant to include the acid, lactone and salt forms. When in salt form, the cation may be selected from alkali metal, ammonium and $C_1$–$C_{20}$ alkyl or alkanolammonium counterions.

Illustrative of beta-hydroxy carboxylic acids are $C_7$–$C_{30}$ acids or salts. Illustrative of this category is salicylic acid as well as the alkali metal and ammonium salts thereof.

The alpha hydroxy carboxylic acids have $C_1$–$C_{25}$ carbon chain length with the following structure:

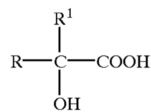

wherein R and $R^1$ are H, F, Cl, Br, alkyl, aralkyl or aryl groups of saturated or unsaturated, isomeric or nonisomeric, straight or branched chain, or cyclic form having 5 or 6 ring members, and in addition, R and $R^1$ may carry OH, CHO, COOH and alkoxy groups having 1 to 9 carbon atoms, the alpha hydroxy acid existing as a free acid or lactone form, or in salt form with an organic amine base or an inorganic alkali, and as stereoisomers, and D, and DL forms when R and $R^1$ are not identical.

Illustrative of this group of materials are 2-hydroxyethanoic acid (glycolic acid); 2-hydroxypropanoic acid (lactic acid); 2-methyl 2-hydroxypropanoic acid (methyllactic acid); 2-hydroxybutanoic acid; 2-hydroxypentanoic acid; 2-hydroxyhexanoic acid; 2-hydroxyheptanoic acid; 2-hydroxyoctanoic acid; 2-hydroxynonanoic acid; 2-hydroxydecanoic acid; 2-hydroxyundecanoic acid; 2-hydroxydodecanoic acid (alphahydroxylauric acid); 2-hydroxytetradecanoic acid (alphahydroxymyristic acid); 2-hydroxyhexadecanoic acid (alphahydroxypalmitic acid); 2-hydroxyoctadecanoic acid (alphahydroxyarachidonic acid); 2-phenyl 2-hydroxyethanoic acid (mandelic acid); 2,2-diphenyl 2-hydroxyethanoic acid (benzilic acid); 3-phenyl 2-hydroxypropanoic acid (phenyllactic acid); 2-phenyl 2-methyl 2-hydroxyethanoic acid (atrolactic acid); 2-(4'-hydroxyphenyl) 2-hydroxyethanoic acid; 2-(4'chlorophenyl) 2-hydroxyethanoic acid; 2-(3'-hydroxy-4'-methoxyphenyl) 2-hydroxyethanoic acid; 2-(4'-hydroxy-3'-methoxyphenyl) 2-hydroxyethanoic acid; 3-(2-hydroxyphenyl) 2-hydroxypropanoic acid; 3-(4'-hydroxyphenyl) 2-hydroxypropanoic acid; and 2-(3',4'-dihydroxyphenyl) 2-hydroxyethanoic acid. Most preferred of this group are glycolic acid, lactic acid, malic acid and 2-hydroxyoctanoic acid and salts thereof.

Levels of the hydroxy carboxylic acids may range from about 0.001 to about 20%, preferably from about 0.1 to about 10%, optimally from about 2 to about 8% by weight of the hydrogel adhesive.

In a particularly preferred embodiment, there will be present a mixture of both a beta hydroxy carboxylic acid and an alpha hydroxy carboxylic acid. For instance, the optimum combination is a mixture of salicylic acid and glycolic acid in a relative weight ratio from about 20:1 to about 1:20, preferably from about 10:1 to 1:1, optimally from about 3:1 to about 2:1.

Advantageously, the hydrogel adhesive will possess a pH ranging from about 1 to about 6.8, preferably from about 2 to about 4.5, optimally from about 2.5 to less than about 4, especially between 2.5 and 3.6.

Dermal adhesive strips of the present invention may be of any size or geometry. The strip may be round, oval, L-shaped, T-shaped, semi-circular, U-shaped or V-shaped. The patch may also be of full-face dimensions with cut-out areas for the eyes, nose and/or mouth.

Strips of the present invention ordinarily will also include a backing layer across the hydrogel adhesive on a side opposite to that of the substrate. Ordinarily the backing layer will be hydrophobic or if hydrophilic will be coated with a hydrophobic coating for quick release from the adhesive. Plastic films are particularly suitable including polyethylene, polyester, polyurethane, polyvinyl chloride, polyamide and metallic foils. The backing film can be a composite or a single layer material. Physically it may appear transparent, opaque, fleshtoned or aluminized.

Skin conditioners, moisturizers and surfactants may be included as additives within the hydrogel adhesive. Illustrative conditioners include mineral oil, petrolatum, vegetable oils (such as soybean or maleated soybean oil), dimethicone, dimethicone copolyol, cationic monomers and polymers (such as guar hydroxypropyl trimonium chloride and distearyl dimethyl ammonium chloride) as well as combinations thereof. Illustrative moisturizers are polyols such as sorbitol, glycerin, propylene glycol, ethylene glycol, polyethylene glycol, polypropylene glycol, 1,3-butane diol, hexylene glycol, isoprene glycol, xylitol, fructose and mixtures thereof.

Surfactants may be those selected from the anionic, cationic, nonionic, amphoteric, zwitterionic and combinations thereof. Most preferred are nonionic and amphoteric surfactants due to their mildness. Examples of suitable amphoterics are cocoamidopropylbetaine and lauroamphoacetate. Particularly suitable nonionics are dialkylamine oxides, alkyl polyglycosides and methyl glucamides. Mild anionic surfactants include salts of sarcosinate, taurate and cocoyl isethionate.

Amounts of the conditioners, moisturizers and surfactants may each independently range from about 0.01 to about 45%, preferably from about 0.1 to about 30%, optimally from about 1 to about 20% by weight for each category.

Skin benefit agents other than the hydroxy acids may also be included in the dermal strips of the present invention. These further additives may be selected from retinoids (e.g. retinol and retinyl linoleate), lipoic acid, ascorbic acid and derivatives thereof, ceramides and pseudoceramides, herbal extracts and combinations thereof. Amounts of these materials may range anywhere from 0.0001 to 5% by weight.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

An adhesive hydrogel is prepared by mixing 30 grams of 2-acrylamido-2-methylpropane sulphonic acid monomer in 20 grams distilled water and 5 grams of a 1% aqueous solution of methylene-bis-acrylamide. The solution is then activated with 0.4% magnesium persulphate catalyst. Shortly after mixing the catalyst with the hydrogel solution, 0.1 grams salicylic acid and 0.1 grams glycolic acid in 5 ml water are added. The resultant solution is coated onto a 50/50 blend of polypropylene and hydrophilic polyester (JVC EW-8092) and allowed to solidify. The resulting deposited hydrogel is warmed for 24 hrs. at 40° C. in a hot air oven. Final water content of the hydrogel is 50%. A polystyrene backing layer is laid over the adhesive hydrogel. L-shaped strips fittable over the eye area are then cut from the resultant cured sheet.

EXAMPLE 2

Another adhesive hydrogel is prepared by mixing 60 grams of polyacrylic acid and 10 grams hydroxyethylmethyacrylate in 30 grams distilled water and 10 grams of a 1% aqueous emulsified solution of glycidyl methacrylate. The solution is then catalyst activated with 0.5% azobisisobutyronitrile. Subsequent to mixing the catalyst with the hydrogel solution, 0.5 grams salicylic acid and 0.5 grams glycolic acid in 20 ml water are added. The resultant solution is coated onto a 60/40 nonwoven blend of polypropylene and hydrophilic rayon and allowed to solidify. Coated substrate is then warmed for 24 hrs. at 40° C. in a hot air oven. Final water content of the hydrogel is 60%. A silicone coated paper backing layer is laid over the adhesive hydrogel. U-shaped strips fittable around the chin area are then cut from the resultant cured sheet.

EXAMPLE 3

Still another adhesive hydrogel of this invention is prepared by mixing 30 grams each of polyvinyl pyrrolidone and polyvinyl alcohol in 20 grams distilled water and 30 grams of a 1% aqueous solution of methylene-bis-acrylamide. The solution is then activated with 0.4% di-tert butyl peroxide. Shortly after mixing the catalyst with the hydrogel solution, 0.1 grams salicylic acid and 5 grams lactic acid in 25 ml water are added. The resultant solution is coated onto a 50/50 blend of low density polyethylene and hydrophilic polyester (JVC EW-8092) and allowed to solidify. Coated substrate is then warmed for 24 hrs. at 40° C. in a hot air oven. Final water content of the hydrogel is 70%. A polypropylene backing layer is laid over the adhesive hydrogel. T-shaped strips fittable over and between the brow area are then cut from the resultant cured sheet.

EXAMPLE 4

Yet another adhesive hydrogel of this invention is prepared by mixing 30 grams polyacrylic acid in 20 grams distilled water and 5 grams of a 1% aqueous solution of ethylene glycol dimethacrylate. The solution is then catalyst activated with 0.4% magnesium persulphate. Following initial activation with the catalyst, 5 grams glycolic acid in 15 ml water is added to the hydrogel solution. Semi-cured solution is coated onto a 30/70 blend of polypropylene and hydrophilic polyester and allowed to solidify. The resulting deposited hydrogel is dried for 24 hrs. at 40° C. in a hot air oven. Final water content of the hydrogel is 60%. A polystyrene backing layer is laid over the adhesive hydrogel. Y-shaped strips fittable over the nose bridge area are then cut from the resultant cured sheet.

EXAMPLE 5

A set of flexible substrates of different fiber constitution were evaluated for two key performance properties. One of these properties was the extent of hydrogel seepage through the non-coated side opposite to the hydrogel. The other was the uniformity of adhesive dispersion across the substrate.

For purposes of the comparative studies, an acrylic hydrogel was employed formulated with 1% salicylic acid and 1% glycolic acid to provide a pH of approximately 3.5.

TABLE I

| Sample No. | 1 | 2 | 3 | 4 | 5 | 6 |
|---|---|---|---|---|---|---|
| | Dupont Sontara 8100 | PGI | Freudenberg EP-4970 | Freudenberg WP-8085 | Freudenberg WO-550 | Freudenberg EW-8092 |
| Fiber Type | Polyester 100% | Polypropylene 100% | Polyester 75% Nylon 25% | Polypropylene 75% Rayon 25% | Hydrophilic Polypropylene 50% Polyester 25% | Polypropylene 50% Polyester 50% |

TABLE I-continued

| Sample No. | 1 | 2 | 3 | 4 | 5 | 6 |
|---|---|---|---|---|---|---|
| | | | | | Rayon 25% | |
| Result when coated with hydrogel | Hydrogel seeped through nonwoven and made the noncoated side tacky. | Material to water repellent. Not compatible with the hydrogel. Could not obtain uniform coating. | Hydrogel seeped through nonwoven and made the noncoated side tacky. | Material too water repellent. Not compatible with the hydrogel. Could not obtain uniform coating. | Hydrogel seeped through nonwoven and made the noncoated side tacky. | Uniform coating. No seep through. |

Polyester utilized in the reported tests were completely formed from hydrophilic fibers. Polypropylene in all samples where it appears except that of Sample No. 5 was of the hydrophobic fiber type. Nylon and rayon were respectively hydrophobic and hydrophilic.

Based on the result in Table I, it is seen that neither 100% hydrophobic nor 100% hydrophilic fiber provides total satisfactory properties. Compare Sample No. 2 to Sample No. 1. Ratios of 3:1 or 1:3 as demonstrated in Samples No. 3 and 4 respectively, were also found lacking. In the first instance, the hydrogel experienced seepage while in the other a non-uniform coating resulted. By contrast, a 50—50 blend of hydrophobic-hydrophilic fiber, as represented in Sample No. 6, resulted in a uniform coating and no seepage was observed through the uncoated side of the substrate.

The foregoing description and examples illustrate selected embodiments of the present invention. In light thereof variations and modifications will be suggested to one skilled in the art, all of which are within the spirit and purview of this invention.

What is claimed is:

1. A dermal adhesive strip comprising:

(i) a flexible substrate formed of hydrophobic and hydrophilic fibers, in a respective ratio of 2:1 to 1:2; and (ii) a hydrogel adhesive deposited on a major surface of the flexible substrate, the adhesive containing an alpha- or beta-hydroxy acid wherein said adhesive is formed from an acrylic acid polymer.

2. The product according to claim 1 wherein the ratio of hydrophobic to hydrophilic fibers is about 1:1.

3. The product according to claim 1 wherein the hydrogel adhesive comprises from about 20 to about 95% water.

4. The product according to claim 1 wherein the hydrogel adhesive comprises from at least 50% to about 80% water.

5. The product according to claim 1 wherein the hydrogel adhesive has a pH ranging from about 1 to about 6.8.

6. The product according to claim 5 wherein the pH ranges from about 2 to about 4.5.

7. The product according to claim 1 wherein the alpha hydroxy acid is selected from the group consisting of lactic acid, glycolic acid, malic acid and mixtures thereof.

8. The product according to claim 1 wherein the beta hydroxy acid is salicylic acid.

9. The product according to claim 1 wherein the adhesive contains a mixture of alpha and beta hydroxy carboxylic acids in a weight ratio from about 20:1 to about 1:20.

10. The product according to claim 1 further comprising a backing layer across the hydrogel adhesive on a side opposite to that of the substrate.

* * * * *